United States Patent [19]

Elbe et al.

[11] Patent Number: 5,278,179
[45] Date of Patent: Jan. 11, 1994

[54] PESTICIDES BASED ON SUBSTITUTED OXAZOLIDINONES, NEW SUBSTITUTED OXAZOLIDINONES, AND THEIR PREPARATION AND USE

[75] Inventors: Hans-Ludwig Elbe, Wuppertal; Stefan Böhm, Leverkusen; Dieter Berg, Wuppertal; Heinz-Wilhelm Dehne, Monheim; Stefan Dutzmann, Hilden, all of Fed. Rep. of Germany

[73] Assignee: Bayer Aktiengesellschaft, Leverkusen, Fed. Rep. of Germany

[21] Appl. No.: 894,402

[22] Filed: Jun. 5, 1992

[30] Foreign Application Priority Data

Jun. 14, 1991 [DE] Fed. Rep. of Germany ....... 4119611

[51] Int. Cl.$^5$ .......................................... C07D 263/20
[52] U.S. Cl. ..................................... 514/376; 548/231
[58] Field of Search ......................... 514/376; 548/231

[56] References Cited

U.S. PATENT DOCUMENTS

| | | | |
|---|---|---|---|
| 3,984,468 | 10/1976 | Klauke et al. | |
| 4,128,654 | 12/1978 | Fugitt et al. | 548/231 |
| 4,340,606 | 7/1982 | Fugitt et al. | 514/376 |
| 4,461,773 | 7/1984 | Gregory et al. | 514/376 |
| 4,487,783 | 12/1984 | Grohe et al. | 564/26 |
| 4,587,217 | 5/1986 | Geigert et al. | 435/135 |
| 4,791,109 | 12/1988 | Clemence et al. | 514/235.2 |
| 4,876,372 | 10/1989 | Nakanishi et al. | 549/329 |
| 5,011,953 | 4/1991 | Nakanishi et al. | 549/529 |

FOREIGN PATENT DOCUMENTS

| | | |
|---|---|---|
| 0050827 | 5/1982 | European Pat. Off. |
| 0072528 | 8/1982 | European Pat. Off. |
| 0091305 | 3/1983 | European Pat. Off. |
| 0275221 | 1/1988 | European Pat. Off. |
| 0287347 | 4/1988 | European Pat. Off. |
| 0368656 | 11/1989 | European Pat. Off. |
| 45-13119 | 5/1970 | Japan ................................... 514/376 |

OTHER PUBLICATIONS

Burger, Medicinal Chemistry, 2d Ed, Interscience, N.Y., p. 42 (1960).
Robert L. Cargill, J. Org. Chem., 1980, pp. 3930–3932.

*Primary Examiner*—Donald G. Daus
*Attorney, Agent, or Firm*—Sprung Horn Kramer & Woods

[57] ABSTRACT

Substituted oxazolidinones, some of which are known, of the formula (I)

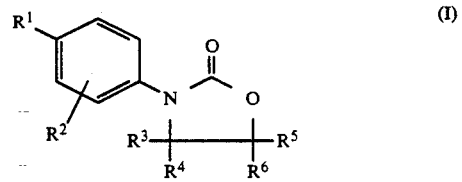

in which
R$^1$ to R$^4$ have the meanings given in the description, are used for combating pests.

The new compounds and those which are known can be prepared by analogous processes by reacting suitable substituted isocyanates with suitable oxiranes or by oxidising suitable oxazolidinones.

7 Claims, No Drawings

PESTICIDES BASED ON SUBSTITUTED OXAZOLIDINONES, NEW SUBSTITUTED OXAZOLIDINONES, AND THEIR PREPARATION AND USE

The invention relates to the use of substituted oxazolidinones, some of which are known, and of new substituted oxazolidinones, a plurality of processes for their preparation, and their use as pesticides.

It has been disclosed that certain substituted oxazolidinones such as, for example, the compound 5-fluoromethyl-3-(4-methylthiophenyl)-1,3-oxazolidin-2-one have fungicidal properties (compare, for example, U.S. Pat. No. 4,128,654).

However, the activity of these previously known compounds is not entirely satisfactory in all fields of application, in particular when low amounts and concentrations are applied.

There are furthermore known certain substituted oxazolidinones such as, for example, the compound 5-chloromethyl-3-(4-trifluoromethylthiophenyl)-1,3-oxazolidin-2-one or the compound 5-chloromethyl-3-(4-trifluoromethylsulphonylphenyl)-1,3-oxazolidin-2-one (compare, for example, EP 50,827). Nothing has been known to date about a pesticidal activity of these previously known compounds.

It has been found that the substituted oxazolidinones, some of which are known, of the general formula (I)

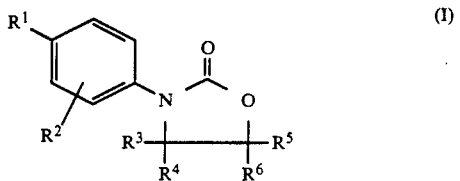

in which
R$^1$ represents trifluoromethylthio, trifluoromethylsulphinyl, trifluoromethylsulphonyl or fluorosulphonyl,
R$^2$ represents hydrogen, cyano, nitro, halogen, alkyl, alkoxy, halogenoalkyl or halogenoalkoxy,
R$^3$ R$^5$ independently of one another in each case represent hydrogen, alkyl, alkenyl, alkinyl, halogenoalkyl or optionally substituted cycloalkyl and
R$^4$ and R$^6$ independently of one another in each case represent hydrogen or alkyl,
have a good activity against pests.

The compounds of the formula (I) may exist in the form of geometric and/or optical isomers or mixtures of isomers of various compositions, depending on the nature of the substituents. The invention claims the use of the pure isomers as well as that of the isomer mixtures. Surprisingly, the substituted oxazolidinones of the general formula (I) which can be used according to the invention show a considerably better activity against phytopathogenic fungi than the oxazolidinones known from the prior art such as, for example, the compound 5-fluoromethyl-3-(4-methylthiophenyl)-1,3-oxazolidin-2-one, which are similar compounds chemically and from the point of view of their action.

Formula (I) provides a general definition of the substituted oxazolidinones which can be used according to the invention. Compounds of the formula (I) in which
R$^1$ represents trifluoromethylthio, trifluoromethylsulphinyl, trifluoromethylsulphonyl or fluorosulphonyl,
R$^2$ represents hydrogen, cyano, nitro, fluorine, chlorine, bromine, iodine, in each case straight-chain or branched alkyl or alkoxy, each of which has 1 to 6 carbon atoms, or in each case straight-chain or branched halogenoalkyl or halogenoalkoxy, each of which has 1 to 6 carbon atoms and each of which has 1 to 13 identical or different halogen atoms,
R$^3$ and R$^5$ independently of one another in each case represent hydrogen, in each case straight-chain or branched alkyl, alkenyl or alkinyl, each of which has up to 6 carbon atoms, or represent straight-chain or branched halogenoalkyl having 1 to 6 carbon atoms and 1 to 13 identical or different halogen atoms, or represent cycloalkyl which has 3 to 7 carbon atoms and which is optionally monosubstituted or polysubstituted by identical or different substituents from the series comprising halogen and/or in each case straight-chain or branched alkyl and/or halogenoalkyl, each of which has 1 to 4 carbon atoms and, if appropriate, 1 to 9 identical or different halogen atoms, and
R$^4$ and R$^6$ independently of one another in each case represent hydrogen or straight-chain or branched alkyl having 1 to 6 carbon atoms,
can preferably be used.

Compounds of the formula (I) in which
R$^1$ represents trifluoromethylthio, trifluoromethylsulphinyl, trifluoromethylsulphonyl or fluorosulphonyl,
R$^2$ represents hydrogen, cyano, nitro, fluorine, chlorine, bromine, in each case straight-chain or branched alkyl or alkoxy, each of which has 1 to 4 carbon atoms, or in each case straight-chain or branched halogenoalkyl or halogenoalkoxy, each of which has 1 to 4 carbon atoms and in each case 1 to 9 identical or different halogen atoms,
R$^3$ and R$^5$ independently of one another in each case represent hydrogen, in each case straight-chain or branched alkyl, alkenyl, or alkinyl, each of which has up to 4 carbon atoms, or represent in each case straight-chain or branched halogenoalkyl having 1 to 4 carbon atoms and 1 to 9 identical or different halogen atoms, or represent cycloalkyl which has 3 to 6 carbon atoms and which is optionally monosubstituted to pentasubstituted by identical or different substituents from the series comprising halogen and/or in each case straight-chain or branched alkyl and/or halogenoalkyl, each of which has 1 to 3 carbon atoms and, if appropriate, 1 to 7 identical or different halogen atoms, and
R$^4$ and R$^6$ independently of one another in each case represent hydrogen or straight-chain or branched alkyl having 1 to 4 carbon atoms,
can particularly preferably be used.

Compounds of the formula (I) in which
R$^1$ represents trifluoromethylthio, trifluoromethylsulphinyl, trifluoromethylsulphonyl or fluorosulphonyl,
R$^2$ represents hydrogen, cyano, nitro, fluorine, chlorine, bromine, methyl, ethyl, n- or i-propyl, methoxy, ethoxy, n- or i-propoxy, trifluoromethyl, difluoromethyl, trifluoromethoxy or difluoromethoxy,
R$^3$ and R$^5$ independently of one another in each case represent hydrogen, methyl, ethyl, n- or i-propyl, n-, i-, s- or t-butyl, vinyl, allyl, ethinyl, propargyl, fluoromethyl, chloromethyl, bromomethyl, or iodomethyl, or represent cyclopropyl or cyclohexyl, each of which is optionally monosubstituted or disubstituted by identical or different substituents from the series comprising fluorine, chlorine, bromine, methyl, ethyl, n- or i-propyl, difluoromethyl or trifluoromethyl, and $R^4$ and $R^6$ independently of one another in each case represent hydrogen, methyl, ethyl, n- or i-propyl, can especially preferably be used.

Specific reference is made to the compounds mentioned in the preparation examples.

Some of the substituted oxazolidinones of the formula (I) which can be used according to the invention are known (compare, for example, EP 50,827).

Substituted oxazolidinones of the formula (I-A)

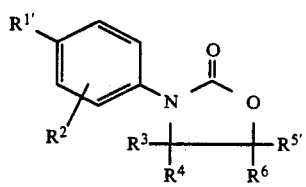
(I-A)

in which $R^{1'}$ represents trifluoromethylthio, trifluoromethylsulphinyl, trifluoromethylsulphonyl or fluorosulphonyl, $R^2$ represents hydrogen, cyano, nitro, halogen, alkyl, alkoxy, halogenoalkyl or halogenoalkoxy, $R^3$ and $R^{5'}$ independently of one another in each case represent hydrogen, alkyl, alkenyl, alkinyl, halogenoalkyl or optionally substituted cycloalkyl and $R^4$ and $R^6$ independently of one another in each case represent hydrogen or alkyl, with the exception of the compounds 5-chloromethyl-3-(4-trifluoromethylthiophenyl)— and 5-chloromethyl-3-(4-trifluoromethylsulphonylphenyl)-1,3-oxazolidin-2-one, were hitherto unknown and are also a subject of the invention.

Known and new substituted oxazolidinones of the formula (I) are obtained when (a) substituted isocyanates of the formula (II)

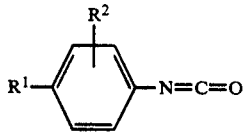
(II)

in which $R^1$ (which includes $R^{1'}$) and $R^2$ have the abovementioned meaning, are reacted with oxiranes of the formula (III)

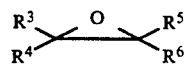
(III)

in which $R^3$, $R^4$, $R^5$ (which includes $R^{5'}$) and $R^6$ have the abovementioned meaning if appropriate in the presence of a diluent and if appropriate in the presence of a reaction auxiliary, or when (b) the substituted oxazolidinones which can be obtained with the aid of preparation process (a), of the formula (Ia)

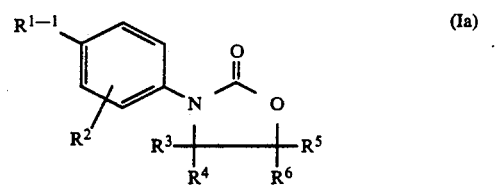
(Ia)

in which $R^{1-1}$ represents trifluoromethylthio and $R^2$, $R^3$, $R^4$, $R^5$ and $R^6$ have the abovementioned meaning, are reacted with an oxidant, if appropriate in the presence of a diluent and if appropriate in the presence of a reaction auxiliary.

If, for example, 4-trifluoromethylthiophenyl isocyanate and epibromohydrin are used as starting substances, the course of the reaction of preparation process (a) can be represented by the following equation:

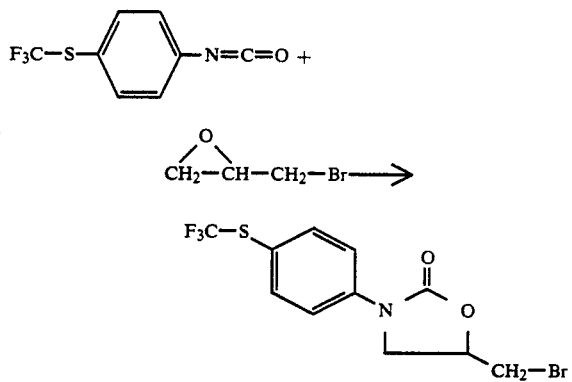

If, for example, 5-bromomethyl-3-(4-trifluoromethylthiophenyl)-1,3-oxazolidin-2-one is used as starting compound and hydrogen peroxide as the oxidant, the course of the reaction of preparation process (b) can be represented by the following equation:

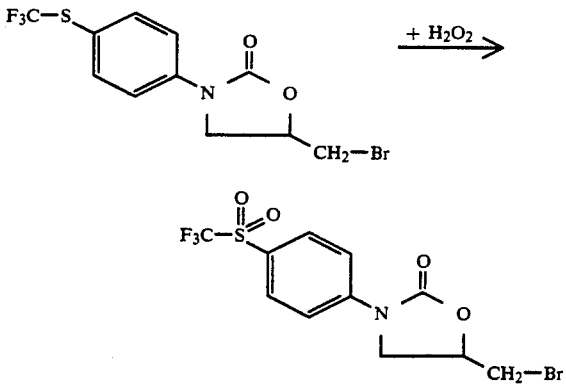

Formula (II) provides a general definition Of the isocyanates required as starting substances for carrying out preparation process (a). In this formula (II), $R^1$ and $R^2$ preferably represent those radicals which have already been mentioned, in connection with the description of the compounds of the formula (I) which can be used according to the invention, as being preferred for these substituents.

The isocyanates of the formula (II) are known or can be obtained analogously to known processes (compare, for example, EP 72,528 equivalent to U.S. Pat. No. 4,487,783; EP 50,827 equivalent to U.S. Pat. No. 4,340,606; DE 2,917,618; DE 2,334,355; ZA 6,804,506,equivalent to U.S. Pat. No. 3,984,468 [1968]; DE 879,550 [1939]).

Formula (III) provides a general definition of the oxiranes furthermore required as starting substances for carrying out preparation process (a). In this formula (III), $R^3$, $R^4$, $R^5$ and $R^6$ preferably represent those radicals which have already been mentioned, in connection with the description of the compounds of the formula (I) which can be used according to the invention, as being preferred for these substituents.

The oxiranes of the formula (III) are generally known or can be obtained analogously to known processes (compare, for example, EP 368,656 equivalent to U.S. Pat. No. 5,011,953; EP 287,347 equivalent to U.S. Pat. No. 4,876,372; U.S. Pat. No. 4,587,217; EP 91,305 equivalent to U.S. Pat. No. 4,587,217; J. Org. Chem. 45, 3930–3932 [1980]; EP 275,221 equivalent to U.S. Pat. No. 4,791,109).

$R^{1'}$ and $R^{5'}$ have the meanings of $R^1$ and $R^5$ which have already been given in the description.

Formula (Ia) provides a general definition of the substituted oxazolidinones required as starting substances for carrying out preparation process (b). In this formula (Ia), $R^2$, $R^3$, $R^4$, $R^5$ and $R^6$ preferably represent those radicals which have already been mentioned, in connection with the description of the compounds of the formula (I) which can be used according to the invention, as being preferred for these substituents.

$R^{1\cdot 1}$ preferably represents a trifluoromethylthio radical. The substituted oxazolidinones are compounds which can be used according to the invention and can be obtained with the aid of preparation process (a).

Suitable diluents for carrying out preparation process (a) are inert organic solvents. These include, in particular, aliphatic, alicyclic or aromatic, optionally halogenated hydrocarbons such as, for example, benzine, benzene, toluene, xylene, chlorobenzene, dichlorobenzene, petroleum ether, hexane, cyclohexane, dichloromethane, chloroform, carbon tetrachloride, ethers such as diethyl ether, diisopropyl ether, dioxane, tetrahydrofuran or ethylene glycol dimethyl ether or ethylene glycol diethyl ether, ketones such as acetone, butanone or methyl isobutyl ketone; nitriles such as acetonitrile, propionitrile or benzonitrile; amides such as N,N-dimethylformamide, N,N-dimethylacetamide, N-methylformanilide, N-methylpyrrolidone or hexamethylphosphoric triamide, esters such as methyl acetate or ethyl acetate, or sulphoxides such as dimethyl sulphoxide.

Preparation process (a) is preferably carried out in the presence of a suitable reaction auxiliary. Reaction auxiliaries which are suitable are, in particular, alkali metal halides. Lithium halides such as, for example, lithium chloride or lithium bromide, are particularly preferably used.

When carrying out preparation process (a), the reaction temperatures can be varied within a substantial range. In general, the process is carried out at temperatures between 50° C. and 150° C., preferably at temperatures between 80° C. and 120° C.

For carrying out preparation process (a), 0.7 to 2.0 moles, preferably 0.9 to 1.25 moles, of oxirane of the formula (III) and, if appropriate, 0.001 to 2.0 moles, preferably 0.01 to 1.0 mole, of reaction auxiliary are generally employed per mole of isocyanate of the formula (II).

The reaction is carried out and the reaction products are worked up and isolated by known processes (compare, in this context, for example U.S. Pat. No. 4,128,654 or the preparation examples).

Oxidants which are suitable for carrying out preparation process (b) are all oxidants which can customarily be used for sulphur oxidations. Hydrogen peroxide or organic peracids such as, for example, peracetic acid, 4-nitroperbenzoic acid or 3-chloroperbenzoic acid, and also inorganic oxidants such as periodic acid, potassium permanganate or chromic acid, are preferably used.

Diluents which are suitable for carrying out preparation process (b) are inorganic or organic solvents, depending on the oxidant used. The following are preferably used: alcohols such as, for example, methanol or ethanol, or mixtures of these substances with water, or pure water; acids such as, for example, acetic acid, acetic anhydride or propionic acid, or dipolar aprotic solvents such as acetonitrile, acetone, ethyl acetate or dimethylformamide, and also optionally halogenated hydrocarbons such as benzine, benzene, toluene, hexane, cyclohexane, petroleum ether, dichloromethane, dichloroethane, chloroform, carbon tetrachloride or chlorobenzene.

If appropriate, preparation process (b) can be carried out in the presence of a reaction auxiliary. Reaction auxiliaries which are suitable are all organic or inorganic acid-binding agents which can customarily be used. The following are preferably used: the hydroxides, acetates or carbonates of alkaline earth metals or alkali metals such as, for example, calcium hydroxide, sodium hydroxide, sodium acetate or sodium carbonate.

If appropriate, preparation process (b) can also be carried out in the presence of a suitable catalyst. Catalysts which are suitable are all those which can customarily be used for sulphur oxidations of this type. Heavy-metal catalysts are preferably used; ammonium molybdate may be mentioned in this connection by way of example.

When carrying out preparation process (b), the reaction temperatures can be varied within a substantial range. In general, the process is carried out at temperatures between −30° C. and +100° C., preferably at temperatures between 0° C. and +80° C.

For carrying out preparation process (b), 2.0 to 10.0 moles, preferably 2.0 to 5.0 moles, of oxidant, if appropriate 1.0 to 1.5 moles, preferably 1.0 to 1.3 moles, of base used as reaction auxiliary and, if appropriate, 0.001 to 1.0 mole, preferably 0.005 to 0.05 mole, of catalyst are generally employed per mole of substituted oxazolidinone of the formula (Ia).

The reaction is carried out and the reaction products are worked up and isolated by known methods (compare, in this context, the preparation examples).

The active compounds which can be used according to the invention have a powerful action against pests and can be employed in practice for combating undesirable harmful organisms. The active compounds are suitable for use as plant protection agents, in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation:

Pythium species, such as, for example, *Pythium ultimum;* Phytophthora species, such as, for example, *Phytophthora infestans;*

Pseudoperonospora species, such as, for example, *Pseudo-peronospora humuli* or *Pseudoperonospora cubensis;*

Plasmopara species, such as, for example, *Plasmopara viticola;*

Peronospora species, such as, for example, *Peronospora pisi* or *P. brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *P. graminea* (conidia form: Drechslera, syn: Helminthosporium);

Cochliobolus species, such as, for example, *Cochliobolus sativus* (conidia form: Drechslera, syn: Helminthosporium);

Uromyces species, such as, for example, *Uromyces appendiculatus;*

Puccinia species, such as, for example, *Puccinia recondita;*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Botrytis cinerea;*

Septoria species, such as, for example, *Septoria nodorum;*

Leptosphaeria species, such as, for example, *Leptosphaeria nodorum;*

Cercospora species, such as, for example, *Cercospora canescens;*

Alternaria species, such as, for example, *Alternaria brassicae* and

Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

In this context, the active compounds which can be used according to the invention can be used with particularly good success for combating cereal diseases such as, for example, against the pathogen causing net blotch disease of barley (*Prenophora teres*) or against the pathogen causing powdery mildew of cereals (*Erysiphe graminis*) or against the pathogen causing spot blotch on barley or wheat (*Cochliobolus sativus*) or against the pathogen causing leaf spot of wheat (*Leptosphaeria nodorum*) or against the pathogen causing snow blight of cereals (*Fusarium nivale*), or for combating diseases in fruit and vegetable growing such as, for example, against the pathogen causing tomato blight (*Phytophthora infestans*) or for combating rice diseases such as, for example, against the pathogen causing rice blast disease (*Pyricularia oryzae*). In this context, the active compounds which can be used according to the invention also show curative properties in addition to protective activity.

Depending on their particular physical and/or chemical properties, the active compounds can be converted to the customary formulations, such as solutions, emulsions, suspensions, powders, foams, pastes, granules, aerosols, very fine capsules in polymeric substances and in coating compositions for seed, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene, or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenohydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds which can be used according to the invention can be present in the formulations as a mixture with other known active compounds such as fungicides, insecticides, acaricides and herbicides, and also as a mixture with fertilisers and growth regulators.

The active compounds can be applied as such, in the form of the formulations or in the use forms prepared from these formulations, such as ready-for-use solutions, suspensions, wettable powders, pastes, soluble powders, dusting agents and granules. They are applied in the customary manner, for example by pouring, spraying, atomising, scattering, dusting, foaming, painting on and the like. It is furthermore possible to apply the active compounds by the ultra-low-volume method or to inject the active compound preparation or the active compound itself into the soil. The seed of the plants can also be treated.

In the treatment of parts of plants, the active compound concentrations in the use forms can be varied within a substantial range: they are generally between 1 and 0.0001% by weight, preferably between 0.5 and 0.001% by weight.

In the treatment of seed, amounts of active compound of 0.001 to 50 g, preferably 0.01 to 10 g, are generally required per kilogram of seed.

In the treatment of the soil, active compound concentrations of 0.00001 to 0.1% by weight, preferably 0.0001 to 0.02% by weight, are required at the site of action.

PREPARATION EXAMPLES

Example 1

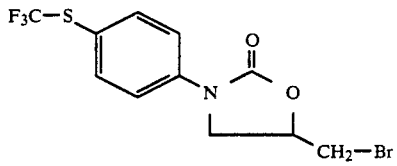

Process a 1 g (0.035 mol) of lithium chloride and 12 g (0.055 mol) of 4-trifluoromethylphenyl isocyanate (compare, for example, EP 50,827) are added in succession to 6.9 g (0.05 mol) of epibromohydrin in 60 ml of dimethylformamide, and the mixture is subsequently stirred for 48 hours at 140° C. For working-up, the cooled reaction batch is poured into water, the mixture is extracted with dichloromethane, and the organic phase is washed twice with water, dried over sodium sulphate concentrated in vacuo. The residue is purified by chromatography on silica gel (mobile phase: diethyl ether).

3.0 g (17% of theory) of 5-bromomethyl-3-(4-trifluoromethylthiophenyl)-1,3-oxazolidin-2-one of melting point 75° C., are obtained.

$^1$H NMR (CDCl$_3$/tetramethylsilane) $\delta = 3.800$; 3.798 ppm.

Example 2

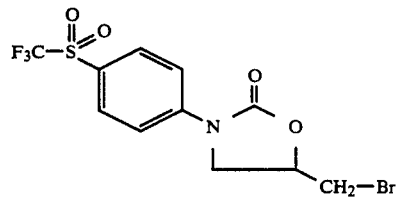

Process b 2 g (0.0056 mol) of 5-bromomethyl-3-(4-trifluoromethylthiophenyl)-1,3-oxazolidin-2-one and 2.2 g (0.023 mol) of 35% strength hydrogen peroxide are added to 10 ml glacial acetic acid and the mixture is stirred for 7 hours at 50° C.; the reaction batch is subsequently poured into water, the supernatant is decanted off, the residue is dissolved in ethyl acetate, the solution is washed with aqueous sodium hydrogen carbonate solution, and the organic phase is dried over sodium sulphate and concentrated in vacuo. The residue can be purified by chromatography on silica gel (eluent: ethyl acetate/cyclohexane 3:1).

1.8 g (83% of theory) of 5-bromomethyl-3-(4-trifluoromethylsulphonylphenyl)-1,3-oxazolidin-2-one are obtained as an oil.

$^1$H NMR (CDCl$_3$/tetramethylsilane) $\delta = 3.840$; 3.824 ppm.

The following substituted oxazolidinones of the general formula (I)

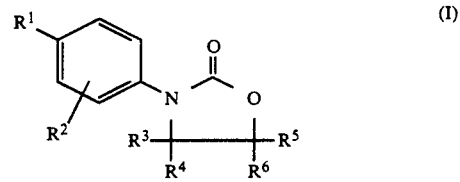

are obtained analogously and following the general preparation instructions:

| Ex. No. | R$^1$ | R$^2$ | R$^3$ | R$^4$ | R$^5$ | R$^6$ | Physical properties |
|---|---|---|---|---|---|---|---|
| 3 | —SCF$_3$ | H | H | H | —CH$_2$—F | H | m.p. 116° C. |
| 4 | —SO$_2$—CF$_3$ | H | H | H | —CH$_2$—F | H | m.p. 82° C. |
| 5 | —SCF$_3$ | H | H | H | —CH$_2$—Cl | H | m.p. 80° C. |
| 6 | —SCF$_3$ | H | H | H | —CH$_2$—I | H | $^1$H NMR*): 3.800; 3.789 |
| 7 | —SO$_2$—CF$_3$ | H | H | H | —CH$_2$—Cl | H | m.p. 97° C. |
| 8 | —SCF$_3$ | H | H | H | —CH$_2$—F | CH$_3$ | m.p. 86° C. |
| 9 | —SO$_2$—CF$_3$ | H | H | H | —CH$_2$—F | CH$_3$ | m.p. 94° C. |
| 10 | —SO$_2$—F | H | H | H | —CH$_2$—F | H | m.p. 123° C. |
| 11 | —SO$_2$—F | H | H | H | —CH$_2$—Cl | H | m.p. 50° C. |
| 12 | —SO$_2$—F | H | H | H | —CH$_2$—Br | H | $^1$H NMR*): 3.84; 3.85 |
| 13 | —SO$_2$—F | H | H | H | —CH$_2$—F | CH$_3$ | $^1$H NMR*): 1.59; 1.60 |

-continued

| Ex. No. | $R^1$ | $R^2$ | $R^3$ | $R^4$ | $R^5$ | $R^6$ | Physical properties |
|---|---|---|---|---|---|---|---|
| 14 | —$SO_2$—F | H | H | H | —$C_2H_5$ | H | $^1$H NMR*): 1.085 |
| 15 | —$SO_2$—F | H | H | H | —$CH_2$—I | H | $^1$H NMR*): 3.83; 3.84 |
| 16 | —$SO_2$—F | H | —$CH_2$—Cl | H | —$CH_2$—Cl | H | m.p. 125° C. |
| 17 | —$SO_2$F | H | H | H | —CH=$CH_2$ | H | m.p. 110° C. |
| 18 | —$SO_2CF_3$ | H | H | H | —CH=$CH_2$ | H | m.p. 127° C. |
| 19 | —$SO_2$—$CF_3$ | H | H | —CH=$CH_2$ | H | H | m.p. 71–72° C. |
| 20 | —$SO_2$—F | H | —$CH_2$—Cl | H | —$CH_2$—Cl | H | m.p. 79–81° C. |

*)The $^1$H NMR spectra were recorded in deuterochloroform (CDCl$_3$) with tetramethylsilane (TMS) as the internal standard. The data indicated are the chemical shift as δ value in ppm.

USE EXAMPLES

In the use examples which follow, the compound listed below was employed as comparison substance:

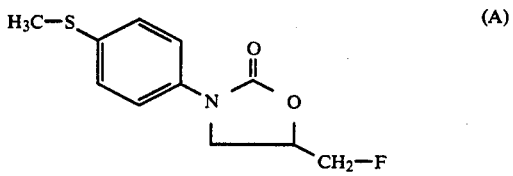

(A)

5-fluoromethyl-3-(4-methylthiophenyl)-1,3=oxazolidin-2-one
(compare, for example, U.S. Pat. No. 4,128,654)

Example A

Phytophthora Test (Tomato)/Protective and Curative

Solvent: 4.7 parts by weight of acetone
Emulsifier: 0.3 parts by weight of alkylaryl polyglycol ether To prepare a suitable preparation of active compound, 1 part by weight of active compound is mixed with the stated amounts of solvent and emulsifier, and the concentrate is diluted with water to the desired concentration.

A1: To test for protective activity, young plants are sprayed with the active compound preparation until dripping wet. After the spray coating has dried on, the plants are inoculated with an aqueous spore suspension of *Phytophthora infestans*.

A2: To test for curative activity, young plants are inoculated with an aqueous spore suspension of *Phytophthora infestans* and remain in an incubation cabin for 7 hours at 20° C. and 100% relative atmospheric humidity. After a brief drying time, the plants are sprayed with the active compound preparation until dripping wet.

The plants are then placed in an incubation cabin at 20° C. and a relative atmospheric humidity of approx. 100%. The test is evaluated 3 days after inoculation.

In this test, a clearly superior activity compared with the prior art is shown, for example, by the compounds of Preparation Examples: 2 and 7.

Example B

Leptosphaeria Nodorum Test (Wheat)/Protective

Solvent: 100 parts by weight of dimethylformamide
Emulsifier: 0.25 parts by weight of alkylaryl polyglycol ether To prepare a suitable preparation of active compound, 1 part by weight of active compound is mixed with the stated amounts of solvent and emulsifier, and the concentrate is diluted with water to the desired concentration.

To test for protective activity, young plants are sprayed with the active compound preparation until dew-moist. After the spray coating has dried on, the plants are sprayed with a spore suspension of *Leptosphaeria nodorum*. The plants remain in an incubation cabin for 48 hours at 20° C. an 100% relative atmospheric humidity.

The plants are placed in a greenhouse at a temperature of approx. 15° C. and a relative atmospheric humidity of approx. 80%.

The test is evaluated 10 days after inoculation.

In this test, a clearly superior activity compared with the prior art is shown, for example, by the compounds of Preparation Examples: 3, 5 and 11.

Example C

Erysiphe Test (Barley)/Protective

Solvent: 100 parts by weight of dimethylformamide
Emulsifier: 0.25 parts by weight of alkylaryl polyglycol ether To prepare a suitable preparation of active compound, 1 part by weight of active compound is mixed with the stated amounts of solvent and emulsifier, and the concentrate is diluted with water to the desired concentration.

To test for protective activity, young plants are sprayed with the active compound preparation until dew-moist. After the spray coating has dried on, the plants are dusted with spores of *Erysiphe graminis* f.sp.

The plants are placed in a greenhouse at a temperature of approx. 20° C. and a relative atmospheric humidity of approx. 80% to favour the development of mildew pustules.

The test is evaluated 7 days after inoculation.

In this test, a clearly superior activity compared with the prior art is shown, for example, by the compounds of Preparation Examples: 2 and 11.

We claim:
1. A method of combating phytopathogenic fungi which comprises applying to such fungi or to a fungus habitat a phytopathogenic-fungi effective amount of a substituted oxazolidinone of the formula

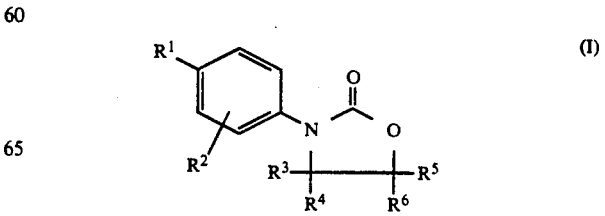

(I)

in which

R¹ represents trifluoromethylthio, trifluoromethylsulphinyl, trifluoromethylsulphonyl or fluorosulphonyl, R² represents hydrogen, or straight-chain or branched alkyl having 1 to 4 carbon atoms, R³ and R⁵ independently of one another in each case represent hydrogen, in each case straight-chain or branched alkyl or alkenyl each of which has up to 4 carbon atoms, or represent in each case straight-chain or branched halogenoalkyl having 1 to 4 carbon atoms and 1 to 9 identical or different halogen atoms, and R⁴ and R⁶ independently of one another in each case represent hydrogen or straight-chain or branched alkyl having 1 to 4 carbon atoms.

2. The method according to claim 1, in which

R¹ represents trifluoromethylthio, trifluoromethylsulphinyl, trifluoromethylsulphonyl or fluorosulphonyl, R² represents hydrogen, methyl, ethyl, n- or i-propyl, R³ and R⁵ independently of one another in each case represent hydrogen, methyl, ethyl, n- or i-propyl, n-, i- or s- butyl, vinyl, allyl, fluoromethyl, chloromethyl, bromomethyl, or iodomethyl, and R⁴ and R⁶ independently of one another in each case represent hydrogen, methyl, ethyl, n- or i-propyl.

3. The method according to claim 1, wherein such compound is 5-bromomethyl-3-(4-trifluoromethyl-sulphonylphenyl)-1,3-oxazolidin-2-one of the formula

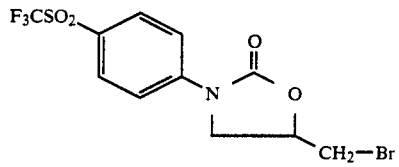

4. The method according to claim 1, wherein such compound is 5-chloromethyl-3-(4-trifluoromethylthiophenyl)-1,3-oxazolidin-2-one of the formula

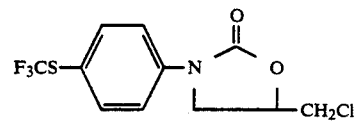

5. The method according to claim 1, wherein such compound is 5-chloromethyl-3-(4-trifluoromethylsulphonylphenyl)-1,3-oxazolidin-2-one of the formula

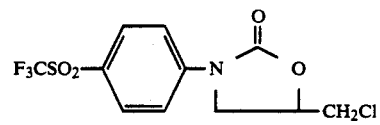

6. A substituted oxazolidinone of the formula

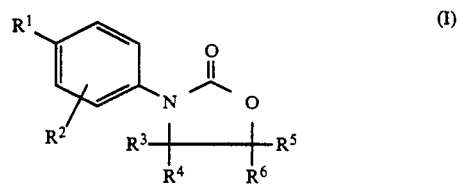

R¹ represents trifluoromethylthio, trifluoromethylsulphinyl, trifluoromethylsulphonyl or fluorosulphonyl, R² represents hydrogen, methyl, ethyl, n- or i-propyl, R³ and R⁵ independently of one another in each case represent hydrogen, methyl, ethyl, n- or i-propyl, n-, i- or s-butyl, vinyl, allyl, fluoromethyl, chloromethyl or bromomethyl, and R⁴ and R⁶ independently of one another in each case represent hydrogen, methyl, ethyl, n- or i-propyl, and their geometric and optical isomers and isomer mixtures, with the exception of the compounds 5-halomethyl-3-(4-trifluoromethylthiophenyl)-, 5-halomethyl-3-(4-trifluoromethylsulphinylphenyl)-1,3-oxazolidin-2-one, and 5-halomethyl-3-(4-trifluoromethylsulphonylphenyl)-1,3-oxazolidin-2-one.

7. A phytopathogenic-fungi effective composition comprising an amount effective therefor of a compound according to claim 6 and a diluent.

* * * * *

UNITED STATES PATENT AND TRADEMARK OFFICE
CERTIFICATE OF CORRECTION

PATENT NO. : 5,278,179
DATED : January 11, 1994
INVENTOR(S) : Elbe, et al.

It is certified that error appears in the above-indentified patent and that said Letters Patent is hereby corrected as shown below:

Line 5, in the Abstract Cancel "$R^1$ to $R^4$" and substitute --$R^1$ to $R^6$--.

Signed and Sealed this

Ninth Day of March, 1999

Attest:

Q. TODD DICKINSON

*Attesting Officer*  *Acting Commissioner of Patents and Trademarks*